US008436222B2

(12) United States Patent
Ghosh et al.

(10) Patent No.: US 8,436,222 B2
(45) Date of Patent: May 7, 2013

(54) PRETREATMENT OF A PHOSPHORUS-MODIFIED ZEOLITE CATALYST FOR AN AROMATIC ALKYLATION PROCESS

(75) Inventors: Ashim Kumar Ghosh, Houston, TX (US); Mohammad Shafiei, Sugar Land, TX (US); Manuel Castelan, Houston, TX (US); Pamela Harvey, Missouri City, TX (US); Neeta Kulkarni, Houston, TX (US)

(73) Assignee: Saudi Basic Industries Corporation, Riyadh (SA)

( * ) Notice: Subject to any disclaimer, the term of this patent is extended or adjusted under 35 U.S.C. 154(b) by 0 days.

(21) Appl. No.: 13/179,987

(22) Filed: Jul. 11, 2011

(65) Prior Publication Data
US 2011/0270008 A1 Nov. 3, 2011

Related U.S. Application Data

(63) Continuation of application No. 12/080,354, filed on Apr. 2, 2008, now Pat. No. 8,115,041.

(51) Int. Cl.
*C07C 2/66* (2006.01)

(52) U.S. Cl.
USPC .......................................... 585/467; 585/906

(58) Field of Classification Search .................. 585/467, 585/466, 906
See application file for complete search history.

(56) References Cited

U.S. PATENT DOCUMENTS

| 3,702,886 | A | 11/1972 | Argauer |
| 3,965,208 | A | 6/1976 | Butter et al. |
| 4,302,621 | A | 11/1981 | Chu |
| 4,456,780 | A | 6/1984 | Young |
| 6,504,072 | B1 | 1/2003 | Brown et al. |
| 6,943,131 | B1 | 9/2005 | Ghosh et al. |
| 7,060,864 | B2 | 6/2006 | Ghosh et al. |
| 7,084,318 | B2 | 8/2006 | Ghosh et al. |
| 7,279,608 | B2 | 10/2007 | Ghosh et al. |
| 7,285,511 | B2 | 10/2007 | Ghosh et al. |
| 7,304,194 | B2 | 12/2007 | Ghosh et al. |
| 2003/0004383 | A1 | 1/2003 | Brown et al. |
| 2005/0240070 | A1 | 10/2005 | Ghosh et al. |
| 2007/0032690 | A1 | 2/2007 | Ghosh et al. |
| 2007/0149384 | A1 | 6/2007 | Ghosh et al. |

OTHER PUBLICATIONS

International Search Report; International Application No. PCT/US09/02028; International Filing Date Apr. 1, 2009; Date of Mailing May 28, 2009; 2 pages.
Written Opinion of the International Searching Authority; International Application No. PCT/US09/02028; International Filing Date Apr. 1, 2009; Date of Mailing May 28, 2009; 4 pages.
Zeolite Definition; Dictionary; http://encarta.msn.com/dictionary_/zeolite.html; Date Accessed: Jul. 29, 2008; 2 Pages.

*Primary Examiner* — Thuan D Dang
(74) *Attorney, Agent, or Firm* — Cantor Colburn LLP

(57) ABSTRACT

This invention relates to a process for pretreating a zeolite catalyst, specifically a zeolite which has been modified with phosphorus. The catalyst may be used in a process for alkylation of aromatics, specifically toluene methylation. The pretreatment is first to contact the catalyst with the process reactants used in a process for alkylation of aromatics for at least two hours at conditions to produce an alkylated aromatic product and then with a gaseous stream containing oxygen at a temperature and for a time until there is no oxygen consumption. The zeolite may be a MFI zeolite. This pretreatment procedure for a phosphorus-modified zeolite catalyst produces a catalyst which has increased run time, i.e., decreased deactivation rate, compared to a fresh catalyst, even after successive regenerations.

12 Claims, 4 Drawing Sheets

Schematic of Toluene Methylation Reaction Unit

Figure 1. Schematic of Toluene Methylation Reaction Unit

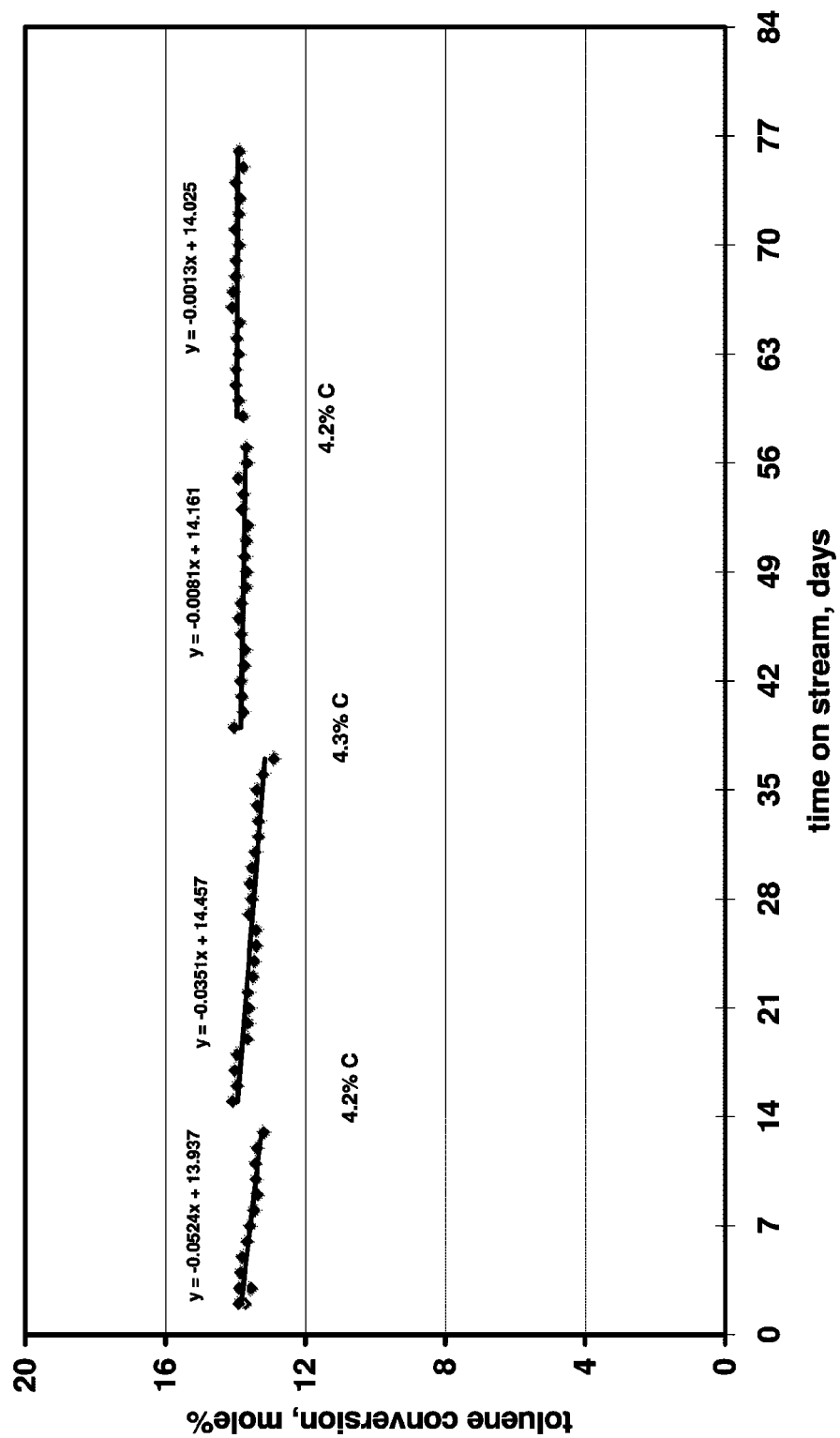

PRETREATMENT OF A PHOSPHORUS-MODIFIED ZEOLITE CATALYST FOR AN AROMATIC ALKYLATION PROCESS

CROSS REFERENCE TO RELATED APPLICATIONS

This application is a continuation of U.S. application Ser. No. 12/080,354 filed Apr. 2, 2008, which is incorporated herein by reference.

BACKGROUND OF THE INVENTION

1. Field of the Invention

This invention relates to a process for alkylation of aromatics, e.g., toluene methylation, with a zeolite catalyst, e.g., an aluminosilicate zeolite which has been modified with phosphorus, said process including pretreatment of the phosphorus-modified zeolite catalyst.

2. Description of the Prior Art

Zeolites are crystalline solids made up of aluminum-substituted $SiO_4$ tetrahedral units joined together to form different ring and cage structures into a crystalline framework. The physical structure of zeolite is very porous with a large internal and external surface area. The substitution of aluminum generates a charge imbalance which must be countered by a supplementary counterion, such as a proton.

Zeolites can be shape-selective catalysts due to steric and electronic effects. Selective reactions can occur over zeolites as certain products, reactants or transition states are kept from forming within the pores either by transition state selectivity or because of size or shape of molecular diameter. By varying the preparation of zeolite catalysts, they can be modified to carry out very specific syntheses of desired products. Elements may be deposited on the zeolite to enhance properties of a zeolite catalyst used in particular processes.

Modified zeolite catalysts are known for alkylation of aromatics, specifically methylation of toluene to xylenes, especially p-xylene Toluene methylation (TM) is a catalytic reaction of toluene with methanol to produce xylenes as shown below:

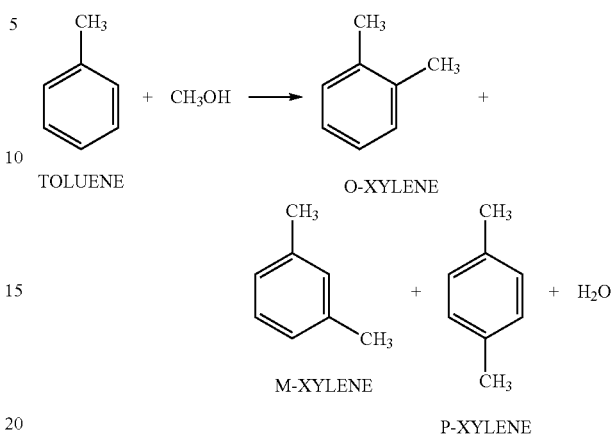

All of these xylene isomers, meta-xylene (m-xylene), ortho-xylene (o-xylene) and para-xylene (p-xylene), are important chemical intermediates. o-Xylene is oxidized to make phthalic anhydride which is used to make phthalate plasticizers among other things. m-Xylene is oxidized to make isophthalic acid, which is used in unsaturated polyester resins (UPR). However, p-xylene has by far the largest market of the three isomers. The largest use of p-xylene is in its oxidation to make terephthalic acid. Terephthalic acid is used in turn to make polymers such as polyethylene terephthalate (PET) and polybutylene terephthalate (PBT). PET is one of the largest volume polymers in the world. As such the demand for p-xylene is several times that for m- and o-xylene. In commercial manufacture p-xylene is purified from mixed xylenes by crystallization and adsorption processes.

Thermodynamic equilibrium compositions of o-, m-, and p-xylenes are approximately 25, 50 and 25%, respectively, at 500° C. The catalytic processes such as toluene dispropor-

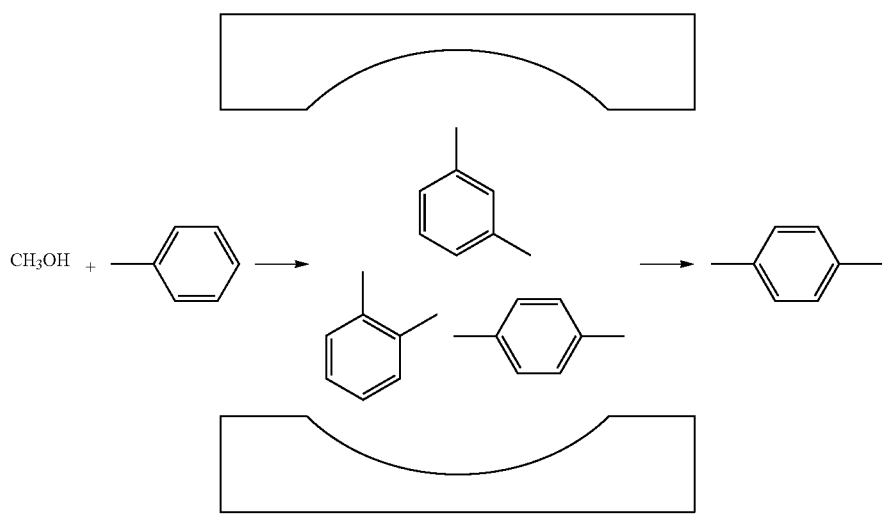

tionation (TDP) and TM would give about 25% p-xylene (PX) in mixed-xylenes (MX). However, if a catalyst possesses shape selective properties it will give significantly greater than 25% PX. Typically, a shape selective catalyst would give >85% PX in MX.

Zeolites as catalysts for isomerization, toluene disproportionation, transalkylation, hydrogenation and alkane oligomerization and aromatization deactivate over time when operated under commercial process conditions and must be regenerated to continue to be used in a reaction system. In zeolite catalysts deactivation is at least in part attributed to the formation of carbonaceous deposits; i.e., "coke", on the active site of the catalyst. Once the coking has affected catalyst performance to the point that product yield is no longer advantageous, the coke must be burned off of the catalyst in an oxygen-containing environment. The regenerated catalyst is then reintroduced into contact with the reactants and run until such time as coking again reduces performance to an unacceptable level. The catalyst is again regenerated and this cycle repeats.

U.S. Pat. No. 4,456,780 discloses a method for pretreatment of a zeolite catalyst with steam and/or a phosphorus-containing compound to decrease coking and extend catalyst life. Pretreatment may be by depositing approximately 4% by weight phosphorus, by contacting the catalyst with steam at 250-1000° C. for 15 minutes to 100 hours or by a combination of phosphorus deposition and steaming.

U.S. Pat. No. 6,504,072 discloses a process for the selective production of para-xylene by reacting toluene with methanol in the presence of a catalyst of a medium-pore zeolite, such as ZSM-5, which has been combined with an oxide modifier, such as phosphorus, and severely steamed at a temperature of at least 950° C. The catalyst may be regenerated after accumulating coke in the toluene methylation reaction by burning off a controlled amount of coke in a partial combustion atmosphere at temperature in the range of from about 400 to about 700° C.

U.S. Pat. No. 3,965,208 discloses a process for the methylation of toluene in the presence of a catalyst of zeolite modified with a Group VA element, such as phosphorus, antimony and arsenic, in an amount of at least 0.5% by weight. The catalyst is regenerated by burning coke from the catalyst in an oxygen-containing atmosphere, such as air, at elevated temperatures. The catalyst is reactivated by passing a vaporized Group VA compound through the catalyst bed. One example of reactivation is to pass an equal volume mixture of toluene and diphenyl phosphine chloride at a temperature of about 250° C. for about one-half hour and then heating in air at 150 cc/minute at about 550° C. for about one-half hour.

It is desirable to extend the process run time between regeneration cycles.

SUMMARY OF THE INVENTION

A phosphorus-modified zeolite catalyst is used in a process for the alkylation of aromatics comprising:
  a) pretreating the phosphorus-modified zeolite catalyst by:
    1) first contacting the catalyst with alkylation process reactants for at least two hours at process conditions to produce an alkylated aromatic product, and
    2) second by contacting the catalyst with a gaseous stream comprising oxygen at a temperature and for a time until there is no oxygen consumption;
  b) contacting the pretreated catalyst with alkylation process reactants at process conditions to produce an alkylated aromatic product; and
  c) recovering an alkylated aromatic product.

It has been found that pretreating a phosphorus-modified zeolite catalyst in such a manner produces a catalyst which has increased run time, i.e., decreased deactivation rate, compared to a fresh catalyst. The process may further comprise:
  d) regenerating the catalyst;
  e) contacting the regenerated catalyst with alkylation process reactants at process conditions to produce an alkylated aromatic product; and
  f) repeating steps d) and e).

The zeolite may be MFI aluminosilicate, e.g., phosphorus-modified ZSM-5. A pretreated catalyst has toluene conversion and p-xylene selectivity which are both greater than 95% of that for the original fresh catalyst, even after successive regenerations.

BRIEF DESCRIPTION OF THE DRAWINGS

A more complete appreciation of the invention and many of the attendant advantages thereof will be readily understood by reference to the following detailed description when considered in connection with the accompanying drawings:

FIG. 4 is a graph of time on stream in days v. toluene conversion for Example 3

DETAILED DESCRIPTION OF THE INVENTION

Figure 1:
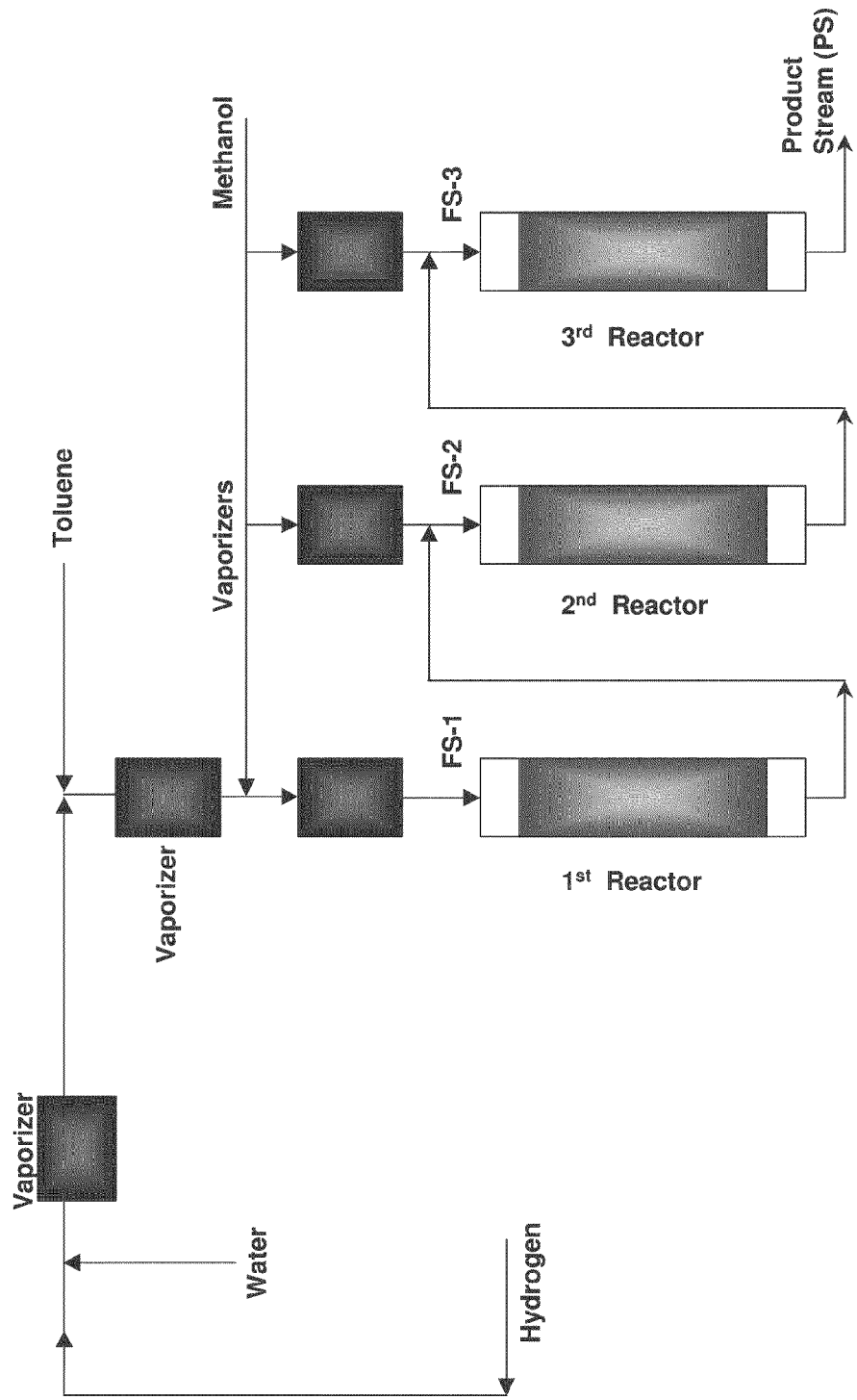
FIG. 1 is a schematic diagram of a toluene methylation reaction unit with reactors in series

Toluene methylation is known to occur over zeolite or zeolite-type catalysts, in particular, ZSM-5-type zeolite catalysts. Generally, a thermodynamic equilibrium mixture of ortho (o)-, meta (m)- and para (p)-xylenes is formed from the methylation of toluene. Thermodynamic equilibrium compositions of o-, m-, and p-xylenes may be around 25, 50 and 25 mole %, respectively, at a reaction temperature of about 500° C. Such toluene methylation may occur over at wide range of temperatures, however.

A high purity grade (99+%) p-xylene is desirable for its oxidation to terephthalic acid process. Thus, an increased concentration of p-xylene over equilibrium is desirable. However, production cost for such a concentration can be very high. p-Xylene can be separated from mixed xylenes by cycle of adsorption and isomerization which must be repeated many times because of its low isomeric concentration in the equilibrium mixture. If the concentration of p-xylene is higher than equilibrium, the high purity grade p-xylene can be more easily attained. An amount of p-xylene significantly higher than equilibrium can be obtained if the catalyst contains shape selective properties. Such shape selective properties can be incorporated in zeolite catalyst by modifying the zeolite.

Zeolite is a crystalline hydrated aluminosilicate that may also contain other metals, such as sodium, calcium, barium, and potassium, and that has ion exchange properties (Encarta® World English Dictionary [North American Edition] © & (P) 2001 Microsoft Corporation). Examples of zeolites are ZSM-5, ZSM-11, ZSM-5/ZSM-11 intermediate, ZSM-12, ZSM-21, ZSM-22, ZSM-23, ZSM-35, ZSM-38, ZSM-48, ZSM-50, MCM-22, Zeolite L, Zeolite Beta and Mordenite which are known in the art.

ZSM-5 zeolite is a porous material containing intersecting two-dimensional pore structure with 10-membered oxygen rings. Zeolites with such 10-membered oxygen ring pore structures are often classified as medium-pore zeolites. As used herein, the expression "ZSM-5-type" is meant to refer to those zeolites that are isostructurally the same as ZSM-5 zeolites. Additionally, the expressions "ZSM-5" and "ZSM-5-type" may also be used herein interchangeably to encompass one another and should not be construed in a limiting sense.

ZSM-5 zeolite catalysts and their preparation are described in U.S. Pat. No. 3,702,886, which is hereby incorporated by reference. In the present invention, the ZSM-5 zeolite catalyst may include those having a silica:alumina molar ratio of at least about 25, of 200 or higher or from about 250 to about 1000 prior to modification. The starting ZSM-5 may be an $NH_4^+$ or $H^+$ form and may contain traces of other cations.

Modification of ZSM-5-type zeolite catalysts with phosphorus-containing compounds has been shown to provide shape selective properties to the catalyst, yielding significantly greater amounts of p-xylene than the thermodynamic equilibrium value when used in toluene methylation compared to unmodified catalysts. Such modification has been shown to provide selectivity for p-xylenes of greater than 80%.

The ZSM-5 may be modified by treating with phosphorus-containing compounds including, but are not limited to, phosphonic, phosphinous, phosphorus and phosphoric acids, salts and esters of such acids and phosphorous halides. In particular, phosphoric acid ($H_3PO_4$) and ammonium hydrogen phosphate (($NH_4)_2HPO_4$) may be used as the phosphorus-containing compound to provide a catalyst for toluene methylation with shape selective properties to provide increased p-xylene selectivity. Such modified catalysts may contain phosphorus (P) in an amount of from about 0.01 to about 0.15 g P/g zeolite, more particularly from about 0.02 to about 0.13 g P/g zeolite, and more particularly from about 0.07 g P/g zeolite to about 0.12 g P/g zeolite, and still more particularly from about 0.09 g P/g zeolite to about 0.11 g P/g zeolite. After phosphorus treatment, the phosphorus-treated zeolite may be dried.

The phosphorus-modified ZSM-5 may be made by forming a slurry of a ZSM-5-type zeolite and an aqueous solution of a phosphorus compound and removing water from the slurry to form a phosphorus-modified ZSM-5 zeolite. The phosphorus-modified catalyst prepared as described in U.S. Pat. No. 7,285,511 issued Oct. 23, 2007, which is hereby incorporated by reference, is not steamed and has a pore volume of from 0.2 ml/g or less.

The phosphorus-modified ZSM-5 may be made by dissolving alumina in a phosphorus-containing acid solution and treating the zeolite with the dissolved alumina solution as described in U.S. Pat. No. 6,943,131 issued Sep. 13, 2005, which is hereby incorporated by reference.

The phosphorus-modified ZSM-5 may have particular $^{31}P$ MAS NMR peaks indicating the present of free phosphate, phosphate bonded to extra-framework aluminum, or particular phosphate species as described in Published U.S. Patent Application no. 2005-0240070 A1 published Oct. 27, 2005, which is hereby incorporated by reference. The catalyst may exhibit at least two $^{31}P$ MAS NMR peaks having maxima at from about 0 ppm to about −55 ppm. More particularly, the catalyst may exhibit a $^{31}P$ MAS NMR peak having a maximum at from about 0 ppm to about −25 ppm, more particularly at from about −5 ppm to about −20 ppm, and another with a maximum at from about −40 ppm to about −50 ppm. Such peaks are an indication of various phosphorus species.

Zeolites other than ZSM-5 which are useful in the present invention are medium pore zeolites that have 10 and/or 12 member ring channels system, such as ZSM-4 (Zeolite Omega), ZSM-11, ZSM-12, ZSM-22, ZSM-23, Zeolite Beta, Mordenite, MCM-22 and combinations and mixtures thereof. Silica-alumina phosphates (SAPO), aluminum phosphates (AlPO) and combinations and mixtures thereof are also useful in the present invention.

The phosphorus-modified zeolite may be heated at 300° C. or higher after phosphorus treatment and then combined with an inorganic oxide binder material to form a zeolite-binder mixture which forms a bound zeolite catalyst as described in Published U.S. Patent Application no. 2007-0032690 A1 published Feb. 8, 2007, which is hereby incorporated by reference.

The phosphorus-modified zeolite catalyst can be combined with an inorganic oxide binder material which has been treated with a mineral acid to form a zeolite-binder mixture and heating the zeolite-binder mixture at temperature of about 400° C. or higher to form a bound zeolite catalyst as described in Published U.S. Patent Application No. 2007-0149384 A1 published Jun. 28, 2007, which is hereby incorporated by reference.

The bound P-modified zeolite catalyst may be mildly steamed at a temperature of 300° C. or lower before using the catalyst in any reaction. The steaming can be carried out in-situ or ex-situ of the reactor. The use of catalyst steaming at mild temperatures is described in co-pending U.S. Pat. No. 7,304,194 issued Dec. 4, 2007, entitled "Hydrothermal Treatment of Phosphorus-Modified Zeolite Catalysts," which is herein incorporated by reference.

The P-modified ZSM-5 catalyst may be contacted with an appropriate feed of alkylation process reactants, such as an aromatic hydrocarbon and an alkylating agent, under process conditions to produce an alkylated aromatic product. The catalyst has particular application for use in toluene methylation utilizing a toluene/methanol feed. As used herein, the expression "alkylation process reactants" is meant to encompass the aromatic compound and the alkylating agent which include toluene and methanol, respectively.

A gas cofeed may also be used with the alkylation process reactants. The cofeed gas may include hydrogen or an inert gas. In addition to any cofeed gas, water that may be in the form of steam may also be introduced into the reactor as cofeed along with the alkylation feed. The water or steam used for the methylation reaction may be introduced with or without hydrogen or inert gas as cofeed with the alkylation feed to the reactor during the start up of the alkylation reaction, or it may be introduced subsequent to initial start up. In either case, liquid water may be added and vaporized prior to its mixing with cofeed gas (if any) and the alkylation feed. The use of water cofeed is described in U.S. Pat. No. 7,060,864 issued Jun. 13, 2006, entitled "Toluene Methylation Process," and in U.S. Pat. No. 7,279,608 issued Oct. 9, 2007, entitled "Toluene Methylation Process with Increased Methanol Selectivity", both of which are herein incorporated by reference.

The reactor pressure for toluene methylation or other aromatic alkylation may vary, but typically ranges from about 10 to about 1000 psig. Reactor temperatures may vary, but typically range from about 400 to about 700° C. In one embodiment of the invention, reactor pressure is from about 20 psig to about 50 psig and reactor temperature is from about 500° C. to about 600° C. Upon introduction of feed into the reactor, the catalyst bed temperature may be adjusted to a selected reaction temperature to effect a desired conversion.

The temperature may be increased gradually at a rate of from about 1° C./min to about 10° C./min to provide the desired final reactor temperature. As used in the examples, reactor temperature refers to the temperature as measured as an average temperature of catalyst bed of the reactor. The zeolite catalyst may be regenerated by contacting the catalyst with an oxygen-containing gas until no oxygen consumption is detected, e.g., at a temperature of about 450° C. to about 700° C. for about one to about twenty hours. One means of oxygen detection is with an oxygen analyzer, such as a paramagnetic oxygen sensor with a lower detection limit of 0.01% by volume. By the term "no oxygen consumption is detected" it is meant to be a level of not more than 0.01% by volume. In one embodiment of the invention, the catalyst is regenerated at a temperature of about 500° C. to about 600° C. for about twelve to about fifteen hours.

The catalyst of the claimed invention may be used in a process for toluene methylation with a startup procedure in which the toluene/methanol feed is introduced into the reactor at a relatively high liquid hourly space velocity (LHSV) with a cofeed of hydrogen for one-half to about 20 hours before running the reactor at a relatively lower LHSV as described in U.S. Pat. No. 7,084,318 issued Aug. 1, 2006, which is herein incorporated by reference.

The reaction may be carried out in a variety of different reactors that are commonly used for carrying out aromatic alkylation reactions. Single or multiple reactors in series and/or parallel are suitable for carrying out the aromatic alkylation. Methanol and/or toluene may be added to the product stream entering the second and subsequent reactors when using multiple reactors in series.

The P-modified ZSM-5 zeolite catalyst, as described herein, has particular application for use in toluene methylation for preparing a xylene product from a feed of toluene and methanol. The catalyst provides increased selectivity for p-xylene when used in toluene methylation. In particular, the catalyst may provide greater than 85%, 90% or 95% paraxylene selectivity when used in toluene methylation. Additionally, in certain instances, greater than 95% of total xylene selectivity may be achieved.

Processes useful for the present invention other than toluene methylation would include aromatic alkylation and transalkylation, toluene disproportionation, methanol to gasoline (MTG) processes and n-paraffin ($C_6$ and higher) cyclization.

The P-modified zeolite catalyst is pretreated by first contacting the catalyst with a feed containing toluene, methanol, hydrogen, water under conditions for a toluene methylation reaction. Alkylated aromatic product may be made during the pretreatment procedure. Contact time is at least about two hours or greater. In one embodiment of the invention, reactor temperature is from about 500° to about 600°. Carbonaceous material (coke) may be deposited on the catalyst during this reaction. Contact times may range from about three hours to about ten days but may be as long as twenty days or one hundred days, depending on the reaction conditions. Contact time may be determined by decline in catalyst activity which may be 50% or less. The carbon (coke) content of the catalyst may be from about 0.5% to about 20% by weight after this first contact in the pretreatment. The catalyst is further pretreated by contacting the catalyst with oxygen until no oxygen consumption is detected, e.g., at a temperature of about 450° C. to about 700° C. for at least two hours. Oxygen may be mixed with other gases, e.g., inert gases, such as nitrogen or steam. The gas flow may be at a flow rate of about one to about ten weight hourly space velocity (WHSV=$h^{-1}$). Catalysts pretreated as above have been found to have improved deactivation rates for aromatic alkylation. The term "deactivation rate" will be used to mean activity decline measured as mole % decrease in toluene conversion during a 24 hour period (mole %/day).

The invention having been generally described, the following examples are given as particular embodiments of the invention to illustrate, but not to limit, the invention and to demonstrate the practice and advantages thereof. It is understood that the examples are given by way of illustration and are not intended to limit the specification or the claims to follow in any manner.

As used herein, catalytic activity can be expressed as the % moles of the toluene converted with respect to the moles of toluene fed and can be defined by the following formulas:

$$\text{Mole \% Toluene Conversion} = [(T_i - T_o)/T_i] \times 100 \quad (1)$$

where, $T_i$ is the number of moles of toluene fed and $T_o$ is the number of moles toluene unreacted.

As used herein, selectivity for mixed xylenes may be expressed as:

$$\text{Mole \% Mixed Xylene Selectivity} = [X_{tx}/(T_i - T_o)] \times 100 \quad (2)$$

where, $X_{tx}$ is the number of moles of mixed (o-, m- or p-) xylenes in the product.

As used herein, selectivity for p-xylene may be expressed as:

$$\text{Mole \% p-Xylene Selectivity} = (X_p/X_{tx}) \times 100 \quad (3)$$

where, $X_p$ is the number of moles of p-xylene.

As used herein, methanol conversion may be expressed as:

$$\text{Mole \% Methanol Conversion} = [(M_i - M_o)/M_i] \times 100 \quad (4)$$

where, $M_i$ is the number of moles of methanol fed and $M_o$ is the number of moles methanol unreacted.

As used herein, methanol selectivity for toluene methylation may be expressed as:

$$\text{Mole \% Methanol Selectivity} = [X_{tx}/(M_i - M_o)] \times 100 \quad (5)$$

where, $X_{tx}$ is the number of moles of mixed (o-, m- or p-) xylenes, $M_i$ is the number of moles of methanol fed and $M_o$ is the number of moles of unreacted methanol.

Catalyst Preparation

P-modified ZSM-5 catalysts were prepared using $NH_4$-ZSM-5 zeolite powder having $SiO_2/Al_2O_3$ mole ratio greater than 250 by treating with P-containing compound and then heating to a maximum temperature of about 550° C. to form a P/ZSM-5 zeolite powder catalyst. The catalysts were bound with 20% alumina as binder and extruded to make 1/16-inch cylindrical shape extruded catalyst. The extruded catalysts were calcined or heated at a maximum temperature of about 550° C. for about five hours. Analyses of two batches of the catalysts are shown in Table 1.

TABLE 1

| Catalyst | Elemental Analysis, wt% | | | | $N_2$ Adsorption | |
|---|---|---|---|---|---|---|
| | $Na_2O$ | $SiO_2$ | $Al_2O_3$ | P | SA, $m^2$/g | PV, cc/g |
| Powder Catalyst A | <0.04 | 79.2 | 0.5 | 9.4 | 211 | 0.13 |
| Extruded Catalyst A | <0.04 | 63.4 | 20.4 | 7.5 | 243 | 0.17 |
| Powder Catalyst B | <0.04 | 76.5 | 0.6 | 10.0 | 185 | 0.11 |
| Extruded Catalyst B | <0.04 | 61.0 | 20.2 | 7.4 | 200 | 0.19 |

EXAMPLE 1

Comparative

Extruded Catalyst A was used in a toluene methylation reaction with a reactor unit containing three reactors in series (see FIG. 1). In each of the reactors 40 g of 1/16-inch extruded catalyst was loaded. The catalyst was dried at 200° C. under hydrogen flow (1500 sccm) for at least one hour. The catalyst was steamed by introducing water vapor (6.5 g/h) with a carrier gas of $H_2$ (1500 sccm) at 200° C. overnight. Reaction feed was introduced as follows: hydrogen rate at 3000 sccm, toluene at 90 g/h, steam at 18.5 g/h, and methanol at 6.8 g/h to the $1^{st}$ reactor. Additional methanol feed was added to $2^{nd}$ and $3^{rd}$ reactors at 5.9 g/h and 4.8 g/h, respectively. The inlet pressure for all three reactors was adjusted to 20 psig. Catalyst bed temperature was adjusted to 530° C., 541° C. and 551° C. for $1^{st}$, $2^{nd}$ and $3^{rd}$ reactor, respectively.

Figure 2:
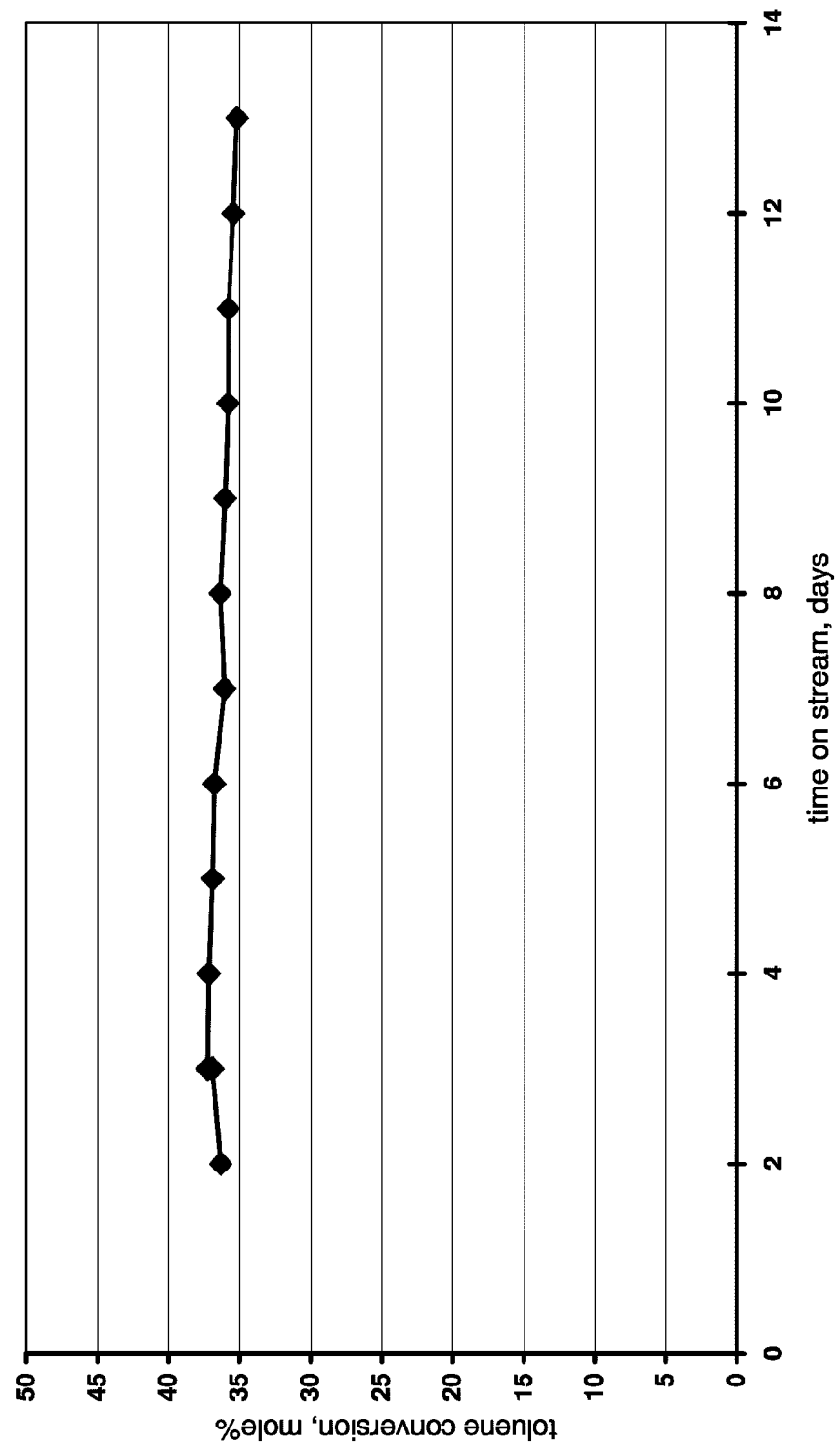
FIG. 2 is a graph of time on stream in days v. toluene conversion for Example 1

Toluene conversion is shown in FIG. 2. In Table 2 included are toluene and methanol conversions, mixed-xylene, p-xylene and methanol selectivities. The activity as measured by toluene conversion was found to decline with time on stream. Toluene conversion was at about 37.3 mole % on day #3 and decreased to 35.2 mole % on day #13 with a decline rate of −0.21 mole % per day.

TABLE 2

| Time on stream, day | Conversion, mole % | | Selectivity, mole% | | |
|---|---|---|---|---|---|
| | Toluene | Methanol | Mixed-Xylene | p-Xylene | Methanol |
| 2 | 36.3 | 94.9 | 91.3 | 92.2 | 60.7 |
| 3 | 37.3 | 95.2 | 93.2 | 92.3 | 63.0 |
| 4 | 37.2 | 94.7 | 93.2 | 92.4 | 63.3 |
| 5 | 36.9 | 94.2 | 93.2 | 92.6 | 63.3 |
| 6 | 36.8 | 93.7 | 93.4 | 92.7 | 63.7 |
| 7 | 36.1 | 93.5 | 93.8 | 92.8 | 62.8 |
| 8 | 36.4 | 93.3 | 93.6 | 92.9 | 63.4 |
| 9 | 36.0 | 92.9 | 93.8 | 93.0 | 63..1 |
| 10 | 35.8 | 93.0 | 94.0 | 93.1 | 62.8 |
| 11 | 35.8 | 92.8 | 93.7 | 93.2 | 62.7 |
| 12 | 35.4 | 92.6 | 94.0 | 93.3 | 62.5 |
| 13 | 35.2 | 92.6 | 94.0 | 93.4 | 62.0 |

EXAMPLE 2

Catalyst Pretreatment

In this example, the catalyst and the conditions for catalyst loading, drying, steaming, and feed introduction to the reactors were the same as described in Example 1. The toluene methylation reaction continued for 3 h at which time the toluene conversion was about 32.7 mole %. The catalyst was determined to have a carbon content (coke) of 0.5% by weight. The methylation reaction was stopped after 3 hours of run, all feeds were stopped, and the catalysts in all three reactors were exposed to controlled flow of oxygen (75 sccm) and nitrogen (1400 sccm). The catalyst in all three reactors was treated in the oxygen environment at a maximum temperature of about 600° C. The consumption of oxygen was measured with a California Analytical Model 602P paramagnetic oxygen sensor with a lower detection limit for oxygen of 0.01% by volume. The pretreatment of catalyst under oxygen and nitrogen flow continued for 12 h at which time no oxygen consumption was detected.

Figure 3:
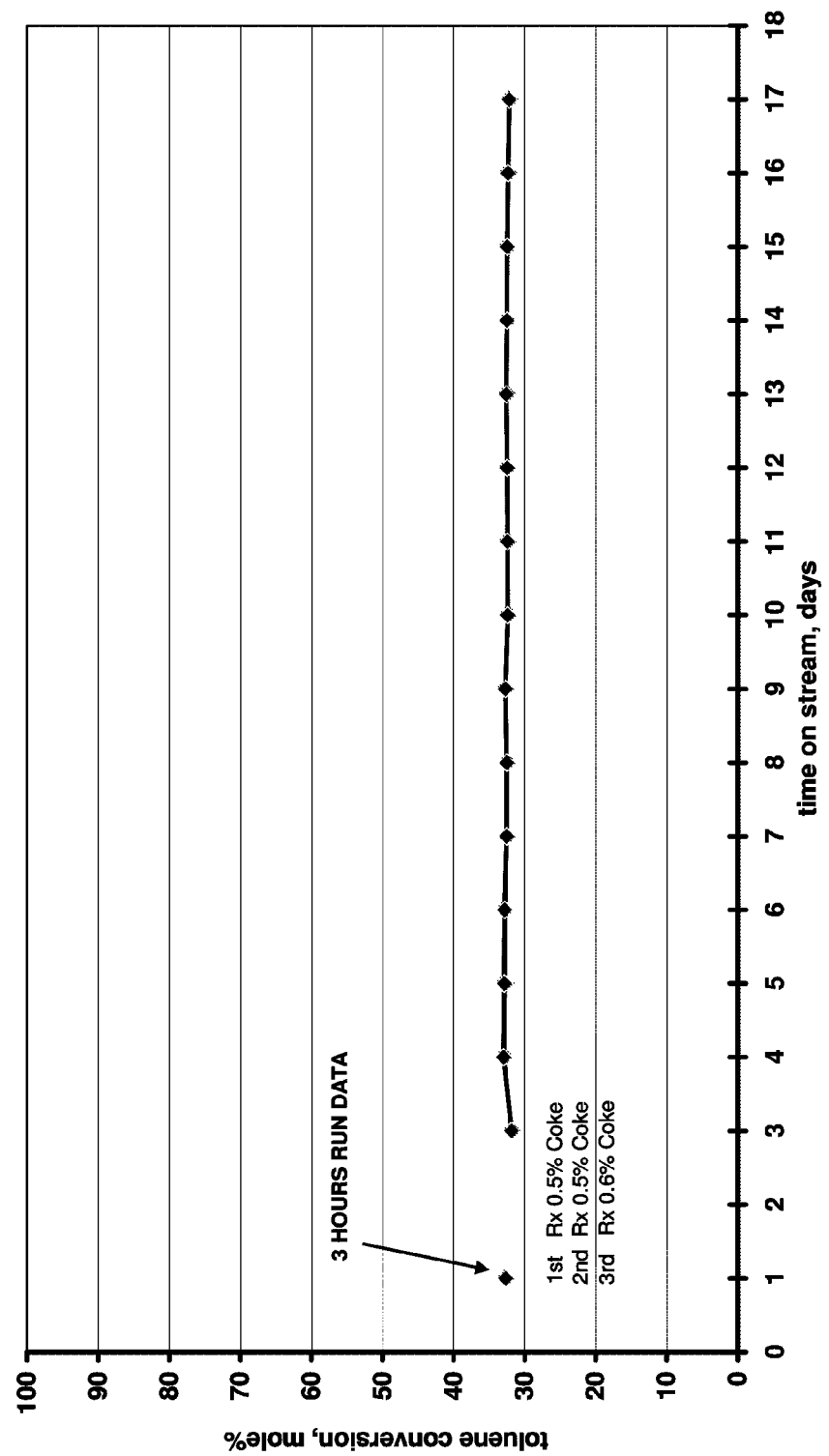
FIG. 3 is a graph of time on stream in days v. toluene conversion for Example 2

The methylation reactants (toluene, methanol) and cofeeds (steam, $H_2$) were reintroduced into the reactors as described earlier. The catalyst bed temperature was adjusted to 530° C., 541° C. and 551° C. for $1^{st}$, $2^{nd}$ and $3^{rd}$ reactor, respectively. Toluene conversions are shown in FIG. 3. In Table 3 included are toluene and methanol conversions, mixed-xylene, p-xylene and methanol selectivities. In the example, toluene conversion was about 31.9 mole % on day #3, 33.0 mole % on day #4 and 32.2 mole % on day #13. Compared to initial toluene conversion (32.7 mole % as noted above) the catalyst showed improved toluene conversion with a deactivation rate of −0.04 mole % per day (compared to −0.21 mole % per day for Example 1).

TABLE 3

| Time on stream, day | Conversion, mole % | | Selectivity, mole % | | |
|---|---|---|---|---|---|
| | Toluene | Methanol | Mixed-Xylene | p-Xylene | Methanol |
| $1^a$ | 32.7 | 98.7 | 95.5 | 91.8 | 56.2 |
| 3 | 31.9 | 97.3 | 95.6 | 92.1 | 55.1 |
| 4 | 33.0 | 94.9 | 95.0 | 92.4 | 58.2 |
| 5 | 32.8 | 93.7 | 95.2 | 92.6 | 59.1 |
| 6 | 32.8 | 93.2 | 95.0 | 92.6 | 59.3 |
| 7 | 32.5 | 93.0 | 95.0 | 92.7 | 59.0 |
| 8 | 32.5 | 92.4 | 95.0 | 92.4 | 58.7 |
| 9 | 32.7 | 91.9 | 95.0 | 92.9 | 59.4 |
| 10 | 32.4 | 91.5 | 95.0 | 93.0 | 59.5 |
| 11 | 32.4 | 91.2 | 94.9 | 93.1 | 59.5 |
| 12 | 32.5 | 90.9 | 94.8 | 93.1 | 59.4 |
| 13 | 32.6 | 90.8 | 94.8 | 93.1 | 59.6 |

$^a$Before catalyst pretreatment

EXAMPLE 3

Catalyst Pretreatment

In this example, to determine catalyst stability in the first reactor, the catalyst and the conditions for catalyst loading, drying, steaming, and feed introduction to the reactors were the same as described in Example 1, except after introduction of the feed, catalyst bed temperature of the first reactor was adjusted to 520° C. The toluene methylation reaction continued for 13 days during which time the toluene conversion was found to decrease at −0.0524 mole % per day. The methylation reaction was stopped after 13 days, all feeds were stopped, and the catalyst in reactor was exposed to controlled flow of oxygen (75 sccm) and nitrogen (1400 sccm). The catalyst bed temperature was 585° C. The consumption of oxygen was measured. The pretreatment of catalyst under oxygen and nitrogen flow continued for 12 h at which time no oxygen consumption was detected.

The methylation reactants (toluene, methanol) and cofeeds (steam, $H_2$) were reintroduced into the reactor as described earlier. The catalyst bed temperature was adjusted to 520° C. The methylation reaction continued until the day #37. Toluene conversions are shown in FIG. 4. In Table 4 included are toluene and methanol conversions, mixed-xylene, p-xylene and methanol selectivities for the first reactor. In the example, the rate of decrease in toluene conversion was found to improve when the catalyst was pretreated under oxygen environment (−0.0351 mole % per day vs. −0.0524 mole % per day for the fresh load catalyst).

The methylation reaction was stopped on day #37, all feeds were stopped, and the catalyst in reactor was exposed to controlled flow of oxygen (75 sccm) and nitrogen (1400 sccm). The catalyst bed temperature was 585° C. The consumption of oxygen was measured. The pretreatment of catalyst with under oxygen and nitrogen flow continued for 12 h at which time no oxygen consumption was detected. The methylation reactants (toluene, methanol) and cofeeds (steam, H2) were reintroduced into the reactor as described earlier. The catalyst bed temperature was adjusted to 520° C. The methylation reaction continued until the day #57. Toluene conversions are shown in FIG. 4. In Table 4 included are toluene and methanol conversions, mixed-xylene, p-xylene and methanol selectivities for the first reactor. In the example, the rate of decrease in toluene conversion was found to improve further when the catalyst was pretreated and subsequently regenerated under oxygen environment (−0.0081 mole % per day vs. −0.0524 mole % per day for fresh catalyst).

The methylation reaction was stopped on day #57, all feeds were stopped, and the catalyst in reactor was exposed to controlled flow of oxygen (75 sccm) and nitrogen (1400 sccm). The catalyst bed temperature was 585° C. The consumption of oxygen was measured. The pretreatment of catalyst with under oxygen and nitrogen flow continued for 12 h at which time no oxygen consumption was detected. The methylation reactants (toluene, methanol) and cofeeds (steam, $H_2$) were reintroduced into the reactor as described earlier. The catalyst bed temperature was adjusted to 520° C. The methylation reaction continued until the day #76. Toluene conversions are shown in FIG. 4. In Table 4 included are toluene and methanol conversions, mixed-xylene, p-xylene and methanol selectivities for the first reactor. In the example, the rate of decrease in toluene conversion was found to improve further when the catalyst was pretreated under oxygen environment (−0.0013 mole % per day vs. −0.0524 mole % per day for fresh load catalyst). Catalyst deactivation is summarized in Table 5.

TABLE 4

| Time on stream, day | Conversion, mole % | | Selectivity, mole % | | |
|---|---|---|---|---|---|
| | Toluene | Methanol | Mixed-Xylene | p-Xylene | Methanol |
| 2 | 13.9 | 94.3 | 63.5 | 95.5 | 97.1 |
| 3 | 13.9 | 93.8 | 63.9 | 95.6 | 97.6 |
| 4 | 13.8 | 93.3 | 63.9 | 95.6 | 97.3 |
| 5 | 13.8 | 92.7 | 64.2 | 95.8 | 97.3 |
| 6 | 13.7 | 92.3 | 64.4 | 95.9 | 97.8 |
| 7 | 13.6 | 92.0 | 64.1 | 95.9 | 97.8 |
| 8 | 13.5 | 91.7 | 63.9 | 96.0 | 97.9 |
| 9 | 13.4 | 91.5 | 64.0 | 96.0 | 98.9 |
| 10 | 13.4 | 91.2 | 63.9 | 96.0 | 97.9 |
| 11 | 13.4 | 90.9 | 64.1 | 96.1 | 97.9 |
| 12 | 13.4 | 90.7 | 64.1 | 96.0 | 97.8 |
| 13 | 13.2 | 90.6 | 63.3 | 96.1 | 97.9 |
| Reaction stopped, catalyst exposed to oxygen environ, feed reintroduced | | | | | |
| 15 | 14.1 | 93.3 | 65.2 | 93.6 | 97.6 |
| 16 | 13.9 | 91.6 | 65.6 | 93.9 | 97.2 |
| 17 | 14.0 | 90.9 | 66.5 | 94.1 | 97.1 |
| 18 | 13.9 | 90.6 | 66.5 | 94.1 | 97.3 |
| 19 | 13.7 | 90.4 | 65.6 | 94.2 | 97.9 |
| 20 | 13.6 | 90.2 | 65.6 | 94.3 | 97.6 |
| 21 | 13.6 | 89.7 | 65.9 | 94.3 | 97.7 |
| 21 | 13.6 | 89.8 | 66.0 | 94.4 | 97.6 |
| 22 | 13.5 | 89.5 | 65.6 | 94.5 | 97.5 |
| 23 | 13.5 | 89.4 | 65.6 | 94.4 | 97.6 |
| 24 | 13.4 | 89.4 | 65.5 | 94.5 | 98.0 |
| 25 | 13.4 | 89.4 | 65.4 | 94.6 | 98.0 |
| 26 | 13.6 | 89.4 | 65.8 | 94.6 | 97.4 |
| 27 | 13.5 | 89.3 | 65.8 | 94.6 | 97.9 |
| 28 | 13.6 | 89.2 | 65.9 | 94.6 | 97.6 |
| 29 | 13.5 | 89.1 | 65.6 | 94.7 | 97.5 |
| 30 | 13.4 | 89.0 | 65.5 | 94.7 | 97.9 |
| 31 | 13.3 | 89.0 | 65.1 | 94.7 | 98.0 |
| 32 | 13.3 | 89.0 | 64.8 | 94.8 | 97.5 |
| 33 | 13.4 | 89.0 | 64.9 | 94.8 | 97.5 |
| 34 | 13.4 | 88.9 | 65.5 | 94.8 | 97.9 |
| 35 | 13.2 | 88.6 | 64.7 | 95.1 | 97.7 |
| 36 | 12.9 | 87.2 | 64.5 | 95.5 | 98.1 |
| 37 | 13.9 | 90.6 | 66.5 | 94.1 | 97.3 |
| Reaction stopped, catalyst exposed to oxygen environ feed reintroduced | | | | | |
| 40 | 13.8 | 89.8 | 66.5 | 93.0 | 97.6 |
| 41 | 13.8 | 89.4 | 66.6 | 93.0 | 97.1 |
| 42 | 13.8 | 88.8 | 66.9 | 93.1 | 96.7 |
| 43 | 13.7 | 88.7 | 66.7 | 93.2 | 97.0 |
| 44 | 13.7 | 88.6 | 66.8 | 93.3 | 97.2 |
| 45 | 13.8 | 88.5 | 66.8 | 93.4 | 96.5 |
| 46 | 13.9 | 88.5 | 67.3 | 93.4 | 96.5 |
| 47 | 13.8 | 88.5 | 67.1 | 93.5 | 96.7 |
| 48 | 13.7 | 88.3 | 66.9 | 93.5 | 96.9 |
| 49 | 13.7 | 88.2 | 67.0 | 93.6 | 97.1 |
| 50 | 13.7 | 88.3 | 67.0 | 93.6 | 96.8 |
| 51 | 13.7 | 88.2 | 67.0 | 93.7 | 97.1 |

TABLE 4-continued

| Time on stream, day | Conversion, mole % | | Selectivity, mole % | | |
|---|---|---|---|---|---|
| | Toluene | Methanol | Mixed-Xylene | p-Xylene | Methanol |
| 52 | 13.6 | 88.4 | 66.9 | 93.7 | 97.2 |
| 53 | 13.8 | 88.3 | 67.3 | 93.8 | 96.6 |
| 54 | 13.8 | 88.3 | 67.3 | 93.8 | 96.7 |
| 55 | 13.9 | 88.4 | 67.8 | 93.8 | 96.7 |
| 56 | 13.7 | 88.0 | 67.0 | 93.9 | 96.8 |
| 57 | 13.7 | 88.0 | 67.3 | 93.9 | 96.8 |
| Reaction stopped, catalyst exposed to oxygen environ, feed reintroduced | | | | | |
| 59 | 13.8 | 91.1 | 65.8 | 92.3 | 97.4 |
| 60 | 13.9 | 90.1 | 66.6 | 92.4 | 96.6 |
| 61 | 14.0 | 89.6 | 67.4 | 92.5 | 96.7 |
| 62 | 14.0 | 89.4 | 67.4 | 92.5 | 96.7 |
| 63 | 13.9 | 89.3 | 67.2 | 92.6 | 96.9 |
| 64 | 14.0 | 89.2 | 67.5 | 92.6 | 96.7 |
| 65 | 13.9 | 89.2 | 67.3 | 92.7 | 96.9 |
| 66 | 14.1 | 89.7 | 67.3 | 92.7 | 96.7 |
| 67 | 14.1 | 89.7 | 67.3 | 92.7 | 96.8 |
| 68 | 14.0 | 89.1 | 67.4 | 92.8 | 96.5 |
| 69 | 14.0 | 89.0 | 67.7 | 92.8 | 96.8 |
| 70 | 13.9 | 89.0 | 67.4 | 92.9 | 97.0 |
| 71 | 14.0 | 89.1 | 67.3 | 92.9 | 96.6 |
| 72 | 13.9 | 89.0 | 67.0 | 93.0 | 97.0 |
| 73 | 13.9 | 89.0 | 66.9 | 93.0 | 97.0 |
| 74 | 14.0 | 89.0 | 67.5 | 93.0 | 96.8 |
| 75 | 13.8 | 88.5 | 66.8 | 93.1 | 96.8 |
| 76 | 13.9 | 88.3 | 67.3 | 93.2 | 96.7 |

TABLE 5

| Catalyst | Run Days | Deactivation Rate (mole %/day |
|---|---|---|
| Fresh | 2-13 | −0.0524 |
| Pretreated | 15-37 | −0.0351 |
| Regenerated | 40-57 | −0.0081 |
| Regenerated | 59-76 | −0.0013 |

EXAMPLE 4

Catalyst Pretreatment

Extruded Catalyst B was used in a toluene methylation unit having three reactors in series (see FIG. 1). Each of the reactors contained approximately 40 g of catalysts and operated at conditions (see Table 6) to convert toluene and methanol to produce xylene products. The catalytic test was conducted for 90 days during which catalysts in the three reactors were pretreated as follows:

$1^{st}$ reactor catalyst—pretreated after 76 days of run.
$2^{nd}$ reactor catalyst—pretreated after 48 days of run
$3^{rd}$ reactor catalyst—pretreated after 33 and regenerated after 67 days of run The catalyst showed a decline in activity, i.e., a decrease in toluene conversion with time on stream. The deactivation rates for fresh load of catalyst in the $1^{st}$, $2^{nd}$ and $3^{rd}$ reactors were −0.025, −0.046 and −0.071 mole %/day, respectively. The catalyst was pretreated by removing coke by contacting with 5.2% $O_2$ with the balance being $N_2$ at a total flow of 1.44 L/min and at a temperature of 550-570° C. for 19 hours. The catalyst showed significantly decreased rates of deactivation after pretreatment (see Table 7). For example, deactivation rate for fresh load catalyst in the $3^{rd}$ reactor was −0.071 mole %/day but after the pretreatment the deactivation rates decreased to −0.058 and after regeneration decreased to −0.026 mole %/day. The results show improved catalyst stability after pretreatment and subsequent regeneration. The results are summarized in Table 7.

TABLE 6

|  | 1st Reactor | 2nd Reactor | 3rd Reactor | Total |
|---|---|---|---|---|
| Days on Stream | 90 | 90 | 90 | |
| Catalyst Loading, g | 40 | 40 | 40 | 120 |
| Reactor Inlet Pressure, psig | 21.7 | 20.7 | 19.8 | |
| Max Temp in Catalyst Bed, °C. | 530 | 540 | 550 | |
| Feed Composition$^a$ | | | | |
| Toluene, g/h | 89.9 | | | 89.9 |
| Methanol, g/h | 7.0 | 5.9 | 5.0 | 17.9 |
| Hydrogen, g/h | 17.4 | | | 17.4 |
| Steam, g/h | 18.2 | | | 18.2 |
| WHSV,$^b$ h$^{-1}$ | 2.4 | 2.0 | 1.7 | |
| LHSV,$^c$ h$^{-1}$ | 2.0 | 1.6 | 1.4 | |
| Toluene Conversion, mole % | 15.7 | 15.6 | 14.3 | 39.0 |
| Methanol Conversion, mole % | 98.3 | 97.6 | 97.4 | 98.1 |
| Mole % Selectivity | | | | |
| Toluene to Mixed-Xylenes | 95.9 | 92.9 | 90.8 | 93.5 |
| Toluene to p-Xylene | 89.7 | 84.4 | 80.3 | 82.6 |
| Methanol to Mixed-Xylene | 68.1 | 65.5 | 57.9 | 64.4 |

$^a$ Feedstreams for 2$^{nd}$ and 3$^{rd}$ reactors contain unconverted toluene and products such xylenes, C9+ aromatics, olefins, etc.
Make-up methanol is added to the 2$^{nd}$ and 3$^{rd}$ reactors.
$^b$ Based on toluene and methanol feed

TABLE 7

| Catalyst in Reactor | Fresh Catalyst Deactivation Rate | Pretreatment* Deactivation Rate | Regeneration* Deactivation Rate |
|---|---|---|---|
| 1$^{st}$ Reactor | −0.025 | | −0.003 |
| 2$^{nd}$ Reactor | −0.046 | −0.021 | |
| 3$^{rd}$ Reactor | −0.071 | −0.058 | −0.026 |

Deactivation rate is defined as the decrease in toluene conversion (mole %/day)
*1st reactor catalyst- pretreated after 76 days of run.
2nd reactor catalyst- pretreated after 48 days of run
3rd reactor catalyst- pretreated after 33 and regenerated after 67 days of run Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letter of Patent of the United States of America is:

1. A process for the alkylation of methylbenzene comprising:
   pretreating a phosphorus-modified zeolite catalyst by contacting the catalyst with alkylation process reactants for at least two hours at process conditions to produce an alkylated aromatic product, and subsequently contacting the catalyst with a gaseous stream comprising oxygen at a temperature and for a time until there is no oxygen consumption;
   contacting the pretreated catalyst with alkylation process reactants at process conditions to produce an alkylated aromatic product; and
   recovering the alkylated aromatic product;
   wherein the alkylation process reactants comprise methylbenzene and methanol; and
   wherein the phosphorus-modified zeolite catalyst comprises a zeolite selected from the group consisting of ZSM-4, Zeolite Beta, Mordenite, MCM-22, and combinations and mixtures thereof.

2. The process of claim 1 wherein the phosphorus-modified zeolite catalyst contains phosphorus in an amount of from about 0.01 to about 0.15 g P/g zeolite.

3. The process of claim 1 wherein the phosphorus-modified catalyst exhibits at least two $^{31}$P MAS NMR peaks having maxima at from about 0 ppm to about −55 ppm.

4. The process of claim 1 wherein the contacting the catalyst with the gaseous stream comprising oxygen at a temperature of about 450° C. to about 700° C. for at least two hours.

5. The process of claim 1 further comprising:
   d) regenerating the catalyst;
   e) contacting the regenerated catalyst with a feedstock comprising toluene and methanol at process conditions to produce an alkylated aromatic product; and
   f) repeating steps d) and e).

6. The process of claim 5, wherein the catalyst is regenerated by contacting the catalyst with an oxygen-containing gas until no oxygen consumption is detected.

7. The process of claim 1, additionally comprising cofeeds with the alkylation process reactants comprising hydrogen and steam.

8. The process of claim 1, wherein the catalyst has an initial deactivation rate before step (a), and a second deactivation rate after step (b), and wherein the initial deactivation rate is greater than the second deactivation rate.

9. A process for pretreating a phosphorus-modified zeolite catalyst comprising contacting the catalyst with alkylation process reactants for at least two hours at process conditions to produce an alkylated aromatic product and then contacting the catalyst with a gaseous stream containing oxygen at a temperature and for a time until there is no oxygen consumption; wherein the alkylation process reactants comprise methylbenzene and methanol; and wherein the phosphorus-modified zeolite catalyst comprises a zeolite selected from the group consisting of ZSM-4, Zeolite Beta, Mordenite, MCM-22, and combinations and mixtures thereof.

10. The process of claim 9, wherein the phosphorus-modified zeolite catalyst contains phosphorus in an amount of from about 0.01 to about 0.15 g P/g zeolite.

11. The process of claim 9, wherein the phosphorus-modified catalyst exhibits at least two $^{31}$P MAS NMR peaks having maxima at from about 0 ppm to about −55 ppm.

12. The process of claim 9, wherein the catalyst is contacted with oxygen at a temperature of about 450° C. to about 700° C. for at least two hours.

* * * * *